US008304239B2

(12) United States Patent
Johnson et al.

(10) Patent No.: US 8,304,239 B2
(45) Date of Patent: Nov. 6, 2012

(54) **DIRECT REGENERATION OF PLANTLETS IN *JATROPHA CURCAS***

(75) Inventors: Tangirala S. Johnson, Maharashtra (IN); Ajay C. Deore, Maharashtra (IN)

(73) Assignee: Reliance Life Sciences PVT Ltd., Navi Mumbai (IN)

( * ) Notice: Subject to any disclaimer, the term of this patent is extended or adjusted under 35 U.S.C. 154(b) by 322 days.

(21) Appl. No.: 12/295,254

(22) PCT Filed: Mar. 30, 2007

(86) PCT No.: PCT/IN2007/000132
§ 371 (c)(1),
(2), (4) Date: Jun. 14, 2010

(87) PCT Pub. No.: WO2008/012832
PCT Pub. Date: Jan. 31, 2008

(65) Prior Publication Data
US 2010/0251421 A1    Sep. 30, 2010

(30) Foreign Application Priority Data
Mar. 31, 2006  (IN) .......................... 490/MUM/2006

(51) Int. Cl.
*C12N 5/00* (2006.01)
*C12N 5/02* (2006.01)
(52) U.S. Cl. ........ 435/410; 435/420; 435/430; 800/295; 800/298
(58) Field of Classification Search .................. 435/410, 435/420, 430; 800/295, 298
See application file for complete search history.

(56) References Cited

U.S. PATENT DOCUMENTS

| 5,538,880 | A | 7/1996 | Lundquist et al. |
| 5,550,318 | A | 8/1996 | Adams et al. |
| 5,610,042 | A | 3/1997 | Chang et al. |
| 7,005,298 | B1 * | 2/2006 | Saxena et al. ................. 435/420 |

FOREIGN PATENT DOCUMENTS

WO    WO-0057690 A2    10/2000

OTHER PUBLICATIONS

Sujatha et al. "Morphogenesis and plant regeneration from tissue cultures of *Jatropha curcas*," Plant Cell, Tissue and Organ Culture, 44: 135-141, 1996.*

Sujatha et al. "Shoot bud proliferation from axillary nodes and leaf sections of non-toxic *Jatropha curcas* L.," Plant Growth Regulation (2005) 47: 83-90.*

Misra et al. "Direct Differentiation of Shoot Buds in Leaf Segments of White Marigold (*Tagetes erecta* L.)," In Vitro Cell. Dev. Biol.-Plant 37: 466-470, 2001.*

Chandran et al., "Isolation and Purification of Protoplasts of Castor (*Ricinus communis* L.) and *Jatropha* spp.",*Gau Res. J.*, 21(2):110-111 (1996).

Datta et al., "In vitro clonal propagation of biodiesel plant (*Jatropha curcas* L.)", *Current Science*, 93(10):1438-1442 (2007).

Gaydou et al., "Energy sources of plant origin in Madagascar: ethyl alcohol and seed oils", *Oleagineux*, 37(3):135-141 (1982) (English Abstract Only).

Gubitz et al., "Exploitation of the tropical oil seed plant *Jatropha curcas* L.", *Bioresource Technol.*, 67:73-82 (1999).

Johri et al., "Morphogenesis in Endosperm Cultures", *Z. Pflanzenphysiol Bd.*, 70(S):285-304 (1973).

Srivastava, P. S., "In vitro Induction of Triploid Roots and Shoots from Mature Endosperm of *Jatropha panduraefolia.*", *Z., Pflanzenphysiol. Bd.*, 66(S):93-96, (1971).

Srivastava, P. S., "Morphogenesis in mature endosperm cultures of *Jatropha panduraefolia"*, *Beitr, Biol. Pflanz.*, 50:255-268 (1974).

Sujatha et al., "Morphogenesis and plant regeneration from tissue cultures of *Jatropha curcas"*, Plant Cell, Tissue & Organ Culture, 44:135-141 (1996).

Sujatha et al., "Morphogenic responses of *Jatropha integerrima* explants to cytokinins", *Biologia*, 55(1):99-104 (2000).

Sujatha et al., "Rapid plant regeneration from various explants of *Jatropha integerrima"*, Plant Cell, Tissue and Organ Culture, 35(3):293-296 (1993).

Sujatha et al., "Shoot bud proliferation from axillary nodes and leaf sections of non-toxic *Jatropha curcas* L ", *Plant Growth Regulation*, 47:83-90 (2005).

Swarup, R., "Biotechnological interventions to improve *Jatropha* seeds and oil quality", SAARC Oils & Fasts Today, pp. 39-41 (Aug. 2004).

Tsugawa et al., "High-frequency transformation of *Lobelia erinus* L by *Agrobacterium*-mediated gene transfer", *Plant Cell Reproduction*, 22:759-764 (2004).

Weida et al., "Induction of callus from *Jatropha curcas* and rapid propagation", *Chinese J. Applied & Environ. Biol.*, 9(2):127-130 (2003) (English Abstract Only).

* cited by examiner

*Primary Examiner* — Susan McCormick Ewoldt
(74) *Attorney, Agent, or Firm* — RatnerPrestia (57) ABSTRACT

This invention provides an efficient process for in vitro propagation of *Jatropha* through direct regeneration of leaf disc without any intermediary callus phase. This process provides a commercially viable process for producing true-to-type plants of *Jatropha* on a large scale and also as a method to produce transgenics through *Agrobacterium*-mediated transformation.

12 Claims, 3 Drawing Sheets

Figure 1: Shows initiation of multiple buds from Jatropha leaf discs.

Figure 2: Shows Multiplication of shoot buds occurring on the surface of leaf discs.

Figure 3: Shows Elongation of induced shoot buds

Figure 4: Shows induction of root in in vitro grown plantlets of Jatropha

Figure 5: Shows micropropagated plant of Jatropa , 2- weeks after acclimatization.

DIRECT REGENERATION OF PLANTLETS IN *JATROPHA CURCAS*

CROSS REFERENCE TO RELATED APPLICATIONS

This application claims the benefit of provisional Indian Application number 490/MUM/2006 filed on Mar. 31, 2006, which is hereby entirely incorporated by reference.

TECHNICAL FIELD OF THE INVENTION

The present invention relates to methods for highly efficient direct regeneration of plantlets through leaf disc of *Jatropha* for producing a commercially viable *Jatropha* plant, mainly for extracting biodiesel from the plant, without any intermediary callus phase. The present invention provides a method for in vitro propagation of *Jatropha* without any intervening callus phase, useful for gene transfer through particle gun or *Agrobacterium*.

BACKGROUND OF THE INVENTION

*Jatropha curcas* is a plant of latin american origin, widely spread throughout the arid and semi-arid tropical regions of the world. *Jatropha* is a large genus comprising over 170 species. The commonly occurring species in india are *j. Curcas, j. Glandulifera, j. Gossypifolia, j. Multifida, j. Nana, j. Panduraefolia, j. Villosa* and *j. Podagrica*.

*Jatropha* is a small tree or shrub with smooth gray bark, which exudes a whitish colored, watery, latex when cut. Normally, it grows between three and five meters in height, but can attain a height of up to eight or ten meters under favorable conditions. It is a drought resistant plant, living up to 50 years and growing on marginal lands. It has large green to pale green leaves, which are aligned alternate to sub-opposite. The leaves are three-five lobed with a spiral phyllotaxis. The petiole of the flowers ranges between 6-23 mm in length. Flowers are formed in hot seasons. In conditions where continuous growth occurs, an imbalance of pistillate or staminate flower production results in a higher number of female flowers. Fruits are produced in winter when the shrub is leafless. Each inflorescence yields a bunch of approximately 10 or more ovoid fruits.

A three, bi-valved cocci is formed after the seeds mature and the fleshy exocarp dries. The seeds become mature when the capsule changes from green to yellow, two to four months after fertilization. The blackish, thin-shelled seeds are oblong and resemble small castor seeds.

This plant has various medicinal uses especially in nutraceuticals, pharmaceutical, dermatological, and personal care products. The latex of *Jatropha curcas* has anticancer properties due to the presence of an alkaloid known as "jatrophine". The tender twigs are used for cleaning teeth. The juice of the leaf is used for external application to treat piles. The roots are used as an antidote for snakebites. The bark yields a dark blue dye used for coloring cloth, fish net and lines.

The seeds are used for anthelmintic purposes. The oil of the seeds has special properties of commercial importance in that it has a very high saponification value and is extensively used for making soaps. Further, it also burns without emitting smoke. Most of these species are ornamental, except for *J. curcas* and *J. glandulifera* that are oil-yielding species (Renu Swamp, 2004. Biotechnological interventions to improve *Jatropha* seeds and oil quality. SAARC Oils & Fats Today, August, pp. 39-41.). The seeds contain semi-dry oil that has been found useful for medicinal and veterinary purposes (Gubitz, G. M; Mittelbach, M and Trabi, M (1999). Exploitation of the tropical oil seed plant *Jatropha curcas* L. Bioresource Technol. Vol. 67, pp. 73-82).

The oil content is 25-30% in the seeds and 50-60% in the kernel. The oil contains 21% saturated fatty acids and 79% unsaturated fatty acids. The *Jatropha* oils are linolenic acid (C18:2) and oleic acid (C18:1) which together account for up to 80% of the oil composition. Palmitic acid (C16:0) and stearic acid (C18:0) are other fatty acids present in this oil. The oil is non-edible, however it has the potential to provide a promising and commercially viable alternative to diesel oil as it has similar desirable physicochemical and performance characteristics as diesel. Of late, the plant *J. curcas* has attracted particular attention as a tropical energy plant. The seed oil can be used as a diesel engine fuel for it has characteristics close to those of the fossil fuel, diesel. Moreover, biodiesel extracted from *Jatropha* meets the European EN 14214 standards for a pure and blended automotive fuel for diesel engines due to its non-toxic and biodegradable nature. *Jatropha curcas* seed yields approach 6-8 MT/ha with ca 37% oil. Such yield can produce the equivalent of 2100-2800 liters of fuel oil/ha, whose energy is equivalent to 19,800-26,400 kwh/ha (Gaydou, A. M; Menet, L; Ravelojaona G and Geneste, P. (1982). Vegetable energy sources in Madagascar: ethyl alcohol and its oil seeds. Oleagineux, Vol 37 (3), pp. 135-141.).

Micropropagation can be defined as in vitro regeneration of plants from organs, tissues, cells or protoplasts using techniques like tissue culture for developing true-to type resultant plants of a selected genotype. In general, tissue from a plant, commonly known as explants, is isolated from a plant whose multiplication is desired to create a sterile tissue culture of that species in vitro. A culture is initiated from the explant. Once a culture is stabilized and growing well in vitro, multiplication of the tissue or regeneration of entire plant can be carried out. Shoots (tips, nodes or internodes) and leaf pieces are commonly used but cultures can be generated from many different tissues. Juvenile tissues generally respond best. Besides the type of explant, the chemical composition of the culture medium and the physical environment of cultures have been found to have great influence on the regeneration capacity, multiplication ratio, and growth and development of new plants in the culture system. Therefore, one needs to find the best suitable factors for individual plant species while maintaining the genotype.

Plant tissue culture is rapidly becoming a commercial method for large-scale propagation of the elite varieties and for plants difficult to propagate rapidly by conventional methods. Tissue culture is particularly useful for multiplication of plants, which are slow growing (turmeric, ginger, cardamom); cross-pollinated (coconut, teak, eucalyptus, cashew, mango and those which show wide variation in the progeny), male sterile lines (cotton, sorghum, pearl millet); and newly virus free plants by meristem culture (sugarcane, potatoes, tapioca, etc).

Known methods of *Jatropha* plant tissue culture have involved passage through the callus stage, which means that there is a high possibility of somaclonal variations. Earlier studies have shown either callus mediated regeneration or direct shoot bud with interspersed callus from hypocotyl, leaves, and petioles. Plant tissue regeneration through a callus stage is vulnerable to somaclonal variations and hence will not ensure true-to-type plants from elite mother plants. Thus, there remains a need for methods that allow propagation of true-to-type *Jatropha* plants.

There is a need to develop a protocol by which *Jatropha* species with desirable traits can be produced. Some of the desirable traits that a *Jatropha* species essentially need producing biofuel are seed yield and oil content in the *Jatropha* species. Other desirable traits are dwarf stem, fatty acid content, early flowering, and synchronous maturity.

Therefore, in view of the above, there is a need to develop tissue culture protocols for the rapid propagation of selected elite variety genotypes of *Jatropha* and for further genetic improvement of *Jatropha*. The present invention is directed towards the rapid propagation of selected elite variety genotypes of *Jatropha* and genetically improved quality of the plant, without any intermediary callus phase and also aims at producing *Jatropha* species with desirable traits.

SUMMARY OF INVENTION

The present invention provides a process for in vitro propagation of *Jatropha* through direct regeneration of leaf discs without any intermediary callus stage, thus avoiding somaclonal variations which often arise during the callus stage.

In one aspect, the invention provides methods for producing a micropropagated true-to-type *Jatropha curcas* plant, including the steps of selecting a leaf from a *Jatropha curcas* plant, isolating a leaf disc from the leaf, and micropropagating the leaf disc in initiation media containing a cytokinin and IBA to produce a micropropagated true-to-type *Jatropha curcas* plant without passing through a callus phase. The cytokinin in the initiation media is preferably zeatin, kinetin, 1-phenyl-3, 1,2,3 thiadiazol-5-yl urea (thiadiziron), or 6 benzyl amino purine (BAP) alone or in combination with each other. In preferred embodiments, the method also includes culturing the leaf discs in proliferation and elongation media containing thidiazuron, BAP, gibberelic acid and IBA; and rooting media containing IBA.

In one embodiment, the present invention provides methods for producing true-to-type *Jatropha curcas* plants including the steps of selecting a leaf from a *Jatropha curcas* plant, isolating a leaf disc from the leaf; and micropropagating the leaf disc in initiation media containing 1-phenyl-3, 1,2,3 thiadiazol-5-yl urea (thidiazuron), 6 benzyl amino purine (BAP), indole butyric acid (IBA). In preferred embodiments, the method also includes culturing the leaf discs in proliferation and elongation media containing thidiazuron, BAP, gibberelic acid and IBA; and rooting media containing IBA to produce a micropropagated true-to-type *Jatropha curcas* plant without passing through a callus phase.

In certain embodiments, the methods include treating the leaf to reduce microbial contamination and/or treating the leaf disc to reduce microbial contamination.

In preferred embodiments, the media contains hormones at particular concentrations. For example, the initiation media may contain thidiazuron at a concentration of about 2.27 µM, BAP at a concentration of about 2.22 µM, and IBA at a concentration of about 0.49 µM. The proliferation and elongation media may contain thidiazuron at a concentration of about 0.22 µM, BAP at a concentration of about 4.44 µM, gibberelic acid at a concentration of about 0.70 µM, and IBA at a concentration of about 0.50 µM. The rooting media may contain IBA at a concentration of about 0.41 µM.

In some embodiments, the selected *Jatropha curcas* plant has a high yield and high oil content. The selected *Jatropha curcas* plant can be either a field grown or micropropagated plant. The micropropagated plant may be propagated from either another micropropagated plant or a field-grown plant. In certain embodiments, the plant is micropropagated by a process including the steps of isolating seeds from a field-grown plant, treating seeds isolated from the field-grown plant to reduce microbial contamination, isolating the embryo and cotyledons from the seeds, and micropropagating the embryo and cotyledons to produce a micropropagated plant. In certain embodiments, the isolated leaf is a young leaf. Preferably, a second leaf, a third leaf, or a fourth leaf, and most preferably, a third leaf.

In another aspect, the present invention provides methods for producing a transgenic *Jatropha curcas* plant by conducting the above-described process for producing true-to-type *Jatropha curcas* plants without passing through a callus phase, and then transforming the isolated leaf disc, and micropropagating the transformed leaf disc in initiation media containing 1-phenyl-3, 1,2,3 thiadiazol-5-yl urea (thidiazuron), 6 benzyl amino purine (BAP), and indole-3-butyric acid (IBA); proliferation and elongation media containing thidiazuron, BAP, IBA, gibberelic acid; and rooting media containing IBA to produce a transgenic *Jatropha curcas* plant without passing through a callus phase. The leaf disc may be transformed using any method known to those of skill in the art, such as particle gun-mediated transformation or *Agrobacterium*-mediated transformation.

In yet another aspect, the invention provides micropropagated true-to-type *Jatropha curcas* plants, resulting from micropropagation of a leaf disc from a *Jatropha curcas* plant in initiation media containing 1-phenyl-3, 1,2,3 thiadiazol-5-yl urea (thidiazuron), 6 benzyl amino purine (BAP), and indole-3-butyric acid (IBA); proliferation and elongation media containing thidiazuron, BAP, IBA, gibberelic acid; and rooting media containing IBA and where the plant does not pass through a callus stage during the micropropagation. Seeds of such a plant and the oil of such seeds are also provided.

In yet another aspect, the invention provides a transgenic *Jatropha curcas* plant, where the plant results from transformation of a leaf disc and micropropagation of the leaf disc in initiation media containing 1-phenyl-3, 1,2,3 thiadiazol-5-yl urea (thidiazuron), 6 benzyl amino purine (BAP), and indole-3-butyric acid (IBA); proliferation and elongation media containing thidiazuron, BAP, IBA, gibberelic acid; and rooting media containing IBA and the plant does not pass through a callus stage during the micropropagation.

In other embodiments, the present invention provides methods for producing true-to-type *Jatropha* plants by steps including, but not limited to: selecting a mother plant and isolating embryos and cotyledons from the dry seeds, culturing embryo and cotyledons to generate complete plantlets, isolating leaf disc from the plantlets and treating to reduce microbial contamination, and micropropagating the leaf disc by culturing in a proliferation and elongation medium, subsequently in a rooting medium, and then hardening the plantlets.

In one embodiment, the present invention provides methods for producing true-to-type *Jatropha* plants by steps including, but not limited to initially selecting a mother plant, collecting dry seeds from a known source which is a high yielding variety, and germinating the seeds in vitro using tissue culture protocols. The isolation of embryo and cotyledons from the dry seeds is done under aseptic conditions. In one preferred embodiment the process involves selecting and treating the mother plant to reduce microbial contamination, e.g., removing any contaminants such as fungus, bacteria, microbes etc., from the surface of seeds after dehusking and their pre-incubation.

In another embodiment the present invention provides methods for producing true-to-type *Jatropha* plants by steps including, but not limited to culturing of embryo and cotyledons to induce complete plantlet in a medium having salts of conventional medium, vitamins of conventional medium, carbon source, phytohormones, and gelling agent. In one preferred embodiment the culturing is done at a pH range of 5.4 to 6.2 in a sterilizing culture medium and incubated at 20-30° C., under cool white fluorescent light and continuing until complete plantlets are formed In certain embodiments, the present invention provides methods for producing true-to type *Jatropha* plants by steps including, but not limited to isolating a leaf from the mother plants from either in vitro germinated seedlings or field grown plants. In one preferred embodiment the method involves isolating a leaf disc from the leaf and treating the leaf disc to reduce microbial contamination by incorporating antibiotics or a combination of antibiotics into the culture media to control bacterial contamination associated with seed borne, inherent contamination.

In one embodiment the present invention provides methods for producing true-to-type *Jatropha* plants by steps including, but not limited to micropropagating the leaf disc by culturing them in a medium capable of inducing shoot buds directly. In one preferred embodiment the medium includes salts of conventional medium, vitamins of conventional medium, carbon source, phytohormones, and gelling agents at a pH range of 5.4 to 6.2 and sterilizing the medium by autoclaving. The cultures may be incubated at 20-35° C. under cool white fluorescent lamps for a minimum period of 2-3 months to induce shoots with sub culturing every 30 days and subsequently cultured in a rooting medium and subjected to hardening.

The present invention thus provides methods which can be used for large-scale propagation of true-to-type *Jatropha* plants, improvement of economic traits, regeneration of leaf discs transformed by particle gun and *Agrobacterium* for pathway engineering of *Jatropha* oil, and as an alternative to exchange and conservation of high-yielding germplasm of *Jatropha*.

BRIEF DESCRIPTION OF THE FIGURES

The following drawings form part of the present specification and are included to further demonstrate certain aspects of the present disclosure, the inventions of which can be better understood by reference to one or more of these drawings in combination with the detailed description of specific embodiments presented herein.

DETAILED DESCRIPTION OF THE INVENTION

Definitions

"Micropropagation" refers to the in vitro regeneration of plants from organs, tissues, cells or protoplasts and the true to type propagation of a selected genotype using in vitro culture techniques.

"Callus" refers to an unorganized or undifferentiated mass of proliferative cells produced either in culture or in nature.

"Gene transfer" refers to incorporation of new DNA into an organism's cells, usually by a vector.

As used herein, the term "transformed" refers to a cell, tissue, organ, or organism into which has been introduced a foreign polynucleotide molecule, such as a construct. Preferably, the introduced polynucleotide molecule is integrated into the genomic DNA of the recipient cell, tissue, organ, or organism such that subsequent progeny inherits the introduced polynucleotide molecule. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule.

"True-to type propagation" means that all characteristics present in mother plant will also be present in next generation, i.e., the plantlets will be the true type of mother plant.

"Genotype" refers to the combination of alleles located on homologous chromosomes that determines a specific characteristic or trait.

"*Agrobacterium* mediated transformation" is the use of *Agrobacterium* to transfer DNA to plant cells harnessed for the purposes of plant genetic engineering.

"Leaf-disc regeneration" refers to direct regeneration of plantlets through leaf disc without passing through the callus stage.

"High yielding germplasm" refers to a process, which conserves genetic material, especially its specific molecular and chemical constitution, which is the physical basis of the inherited qualities of an organism.

"Somaclonal variations" refers to the genetic variability, which can arise during tissue culture.

A "high-yield" *Jatropha curcas* plant is one having an increased number and/or weight of seeds per plant as compared to the average plant. For example, *Jatropha curcas* with yield of approximately 3 kg of seeds per plant is considered to be a high yield plant.

A "high oil content" *Jatropha curcas* plant is one having seeds with increased oil content. For example, *Jatropha curcas* having seeds with 38% oil content is considered to be a "high oil content" plant.

The term "treatment to reduce microbial contamination" refers to common methods known in the art for reducing the level of bacteria and fungi that can interfere with the micropropagation process. These methods can include, but are not limited to, cleaning with detergents or spraying with fungicides, insecticides, pesticides, and other surface-sterilizing agents.

The term "elite variety" refers to any type of plant having characteristics that are desirable. For example, a high yield plant having seeds with high oil content is desirable for the use of *Jatropha* for oil production.

General

The present invention provides a process for in vitro propagation from leaf discs, an easily obtainable explant of *Jatropha*. This method is useful for obtaining plantlets without intermediary callus phase. The present invention also provides true-to-type *Jatropha* and transgenic *Jatropha* made using methods of this invention.

Specifically, the present invention has demonstrated that the use of certain cytokinins and auxins in the initiation media can be used to generate true-to-type *Jatropha* and transgenic *Jatropha* from leaf explants. The cytokinin in the initiation media is preferably zeatin, kinetin, 1-phenyl-3, 1,2,3 thiadiazol-5-yl urea (thiadiziron), or 6 benzyl amino purine (BAP) alone or in combination with each other. The auxin in the initiation media is preferably indole butyric acid (IBA). In particularly preferred embodiments, TDZ and BAP in combination with IBA are used in the initiation media.

The present invention has demonstrated that TDZ (1-phenyl-3-(1,2,3-thiadiazol-5-yl) urea) is able to induce diverse morphogenic responses, ranging from tissue proliferation to adventitious shoots. The ability of TDZ to induce high-shoot regeneration efficiency in woody plant tissues has been reported (Huetteman and Preece, 1993; Meng et al., 2004). In strawberry leaf tissues TDZ in combination with IBA induced high frequency shoot induction (Landi and Mezzetti, 2006). However, strawberry and *Jatropha* are from different families. The present results support the role of TDZ in high-frequency shoot regeneration from *J. curcas* leaf discs.

This invention is not bound by any particular theory. However, it is believed that the ability of TDZ to induce high-frequency shoot regeneration is based on the following mechanism. TDZ is a cytokinin, but there is also evidence that TDZ is a modulator of endogenous auxin levels. There is experimental evidence that TDZ stimulates de novo synthesis of auxins by increasing the levels of indole-3-acetic acid (IAA) and its precursor, tryptophan (Murthy et al., 1995). Increases in endogenous auxin, cytokinin and ethylene have been seen in response to TDZ treatment (Murthy et al., 1995). These effects could explain the high shoot regeneration efficiency observed in *Jatropha* leaf discs. TDZ has been shown to be useful for rapid plant regeneration in several species through organogenesis (Malik and Saxena, 1992).

The methods for producing a true-to-type *Jatropha curcas* may have steps including, but not limited to, selecting a mother plant, preparing the mother plant, isolating a leaf disc from the leaf, treating the leaf disc to reduce microbial contamination, and micropropagating the leaf disc in media containing specified combinations of hormones.

In some embodiments, the mother plant is a field grown plant. In other embodiments, the mother plant is a micropropagated plant.

The methods for producing transgenic *Jatropha curcas* have steps including those described above with the additional step of transforming the leaf disc.

Selection of a Field-Grown or Micropropagated Mother Plant

The mother plant can be either a field-grown plant or a plant micropropagated from another plant. The *Jatropha curcas* mother plants to be used in methods of this invention are selected using methods known to those of skill in the art. In preferred embodiments, healthy plants are selected. Health may be determined by assessing the plants for their size, weight, general growth, appearance, and absence of infection or contamination.

When the mother plant is to be used in a method for production of true-to-type *Jatropha curcas*, elite variety plants are preferred. Elite variety plants are those having desirable traits, such as dwarf stem, early flowering, and synchronous maturity. In preferred embodiments, the elite variety plants are those with high yield and high oil content.

Krikorian (1982) observed that juvenile plant tissues and organs, especially, seedling parts are highly responsive compared to mature, differentiated tissues. In case of *J. curcas*, leaf explants from 2-month-old in vitro seedlings exhibit great propensity for direct regeneration. The present invention has found that leaves taken from mature field grown plants exhibited less morphogenic potential than in vitro seedlings. However, both field-grown and micropropagated plants can be used in this invention.

Micropropagation of a Mother Plant to be Used as a Source for Leaf Discs

In the preferred embodiments, a micropropagated mother plant instead of a field-grown plant is used as a source of leaf discs in order to reduce the likelihood of contamination during methods of the invention. The micropropagated plant may be generated from another micropropagated plant or a field-grown plant.

A micropropagated mother plant can be generated from a field-grown plant by methods including the following steps: isolating seeds from a field-grown plant; reducing the microbial contamination of the seeds isolated from the field-grown plant; isolating the embryo and cotyledons from the seeds; and culturing the embryo and cotyledons to produce plantlets.

A typical procedure includes the following steps. Dry seeds are collected from a known source using methods known to those of skill in the art. If to be used in a method for production of true-to-type plants, the source is preferably an elite variety. The seeds are dehusked and then microbial contamination of the seed surface is reduced using standard methods known in the art, including those described herein for reducing the microbial contamination of mother plants and explants. Embryo and cotyledons are then isolated from the dry seeds under aseptic conditions and cultured in media capable of inducing complete plantlets from the embryo and cotyledons. The media typically includes a standard concentration of salts and vitamins, a carbon source, phytohormones, gelling agent, antibiotics to control bacterial contamination associated with seed borne, inherent contamination, is at a pH ranging from 5.4 to 6.2, and has been sterilized by autoclaving. Common phytohormones used for micropropagation are described herein. The cultures are typically incubated at temperatures between 20 and 30° C. under cool, white fluorescent light. Once complete plantlets are formed, very young leaves can be isolated from the in vitro germinated seedlings and leaf discs are isolated using methods known in the art.

Preparation of Mother Plants

Before leaf discs are isolated, mother plants should be treated to reduce microbial contamination.

Microbial contamination of mother plants can be reduced by spraying the plants with agents such as fungicides, insecticides, pesticides or the like. Preferred fungicides for the pretreatment of the mother plant include Bavistin™, Captan™, Dithane™, Thiram™, Thiovit™, or combinations thereof at a concentration of about 0.05% to 0.2%. Preferred insecticides for the pretreatment of the mother plant include, but are not limited to, Rogor™, Nuvacron, Fastac™, Ultracid™ 40-WP, Thiodane™ at a concentration of about 0.005% to 0.02%.

Isolation and Preparation of Leaf Discs

Leaf discs used in this invention for micropropagation of *Jatropha* may be isolated from either a field grown or micropropagated mother plant.

Isolation of Leaf Discs

The leaf discs are isolated from leaves of the selected mother plants. In preferred embodiments, leaf discs are isolated from young leaves, such as the second, third, or fourth leaf of the selected mother plant. In particularly preferred embodiments, the leaf disc is isolated from the second and third leaves.

Preferably, the leaf discs used as explants in the present invention are selected from the above healthy, fresh, disease-free mother plants.

Reduction of Microbial Contamination of Leaf Discs

Microbial contamination of the leaf discs can be reduced by standard methods such as cleaning and sterilization. Cleaning can be performed using methods known to those of skill in the art, for example, by shaking explants in dilutions of a mild detergent, such as Tween-20. Microbial contamination can be reduced using any method known to those of skill in the art, for example, by treatment with fungicide, a surface sterilizing agent, or combinations thereof. The explant may be subjected to a single round of treatment or multiple rounds of treatment. For example, the explant may go through a primary treatment with the fungicide Bavistin and then go through a secondary treatment with a surface sterilizing agent like sodium hypochlorite or mercuric chloride.

Micropropagation of Leaf Discs

After isolation from a mother plant, leaf discs are micropropagated to produce true-to-type *Jatropha* which have not passed through a callus stage. In certain embodiments, the leaf discs are transformed with a desired gene before micropropagation.

The present invention provides a method for efficient in vitro mass culture of *Jatropha curcas* using leaf discs and culture initiation media containing a cytokinin and IBA to produce the micropropagated true-to-type *Jatropha curcas* plant without passing through a callus phase. The cytokinin in the initiation media is preferably zeatin, kinetin, 1-phenyl-3, 1,2,3 thiadiazol-5-yl urea (thidiziron), or 6 benzyl amino purine (BAP) alone or in combination with each other. In preferred embodiments, the method also includes culturing the leaf discs in proliferation and elongation media containing thidiazuron, BAP, gibberelic acid and IBA; and rooting media containing IBA. In particularly preferred embodiments, the initiation media contains 1-phenyl-3, 1,2,3 thiadiazol-5-yl urea (thidiazuron), 6 benzyl amino purine (BAP), indole butyric acid (IBA); the proliferation and elongation media contains thidiazuron, BAP, gibberelic acid and IBA; and the rooting media contains IBA.

Other aspects of the micropropagation process can be performed using methods known to those of skill in the art in plant tissue culture. Micropropagation typically involves the following steps: 1) culturing explants in initiation media to generate multiple shoots, 2) transferring shoots to proliferation and elongation media, 3) transferring the elongated shoots to rooting media, 4) hardening the plantlets, and 5) transferring the hardened plantlets to the field.

General Media Composition

The media for micropropagation typically includes a standard concentration of salts and vitamins, a carbon source, gelling agent, antibiotics to control bacterial contamination associated with seed borne, inherent contamination, is at a pH range of 5.4 to 6.2, and has been sterilized. The cultures are typically incubated at 20-35° C. under cool, white fluorescent lamps for a minimum period of 2-3 months to induce shoots with sub-culturing every 30 days.

The basal media used to culture *Jatropha* can be any of those already known in the field of the art for plant tissue culture, such as Murashige & Skoog, Gamborg's, Vacin & Went, White's, Schenk & Hildebrandt or the like.

In some embodiments, the proliferation and shoot elongation medium and rooting medium have the same level of nutrients as the initiation medium. In other embodiments, the compositions are similar but not precisely the same.

The basal media can be supplemented with various carbon sources. The carbon source may be sucrose or glucose, typically, at a concentration of about 2-5%. The carbon source may also be sugar alcohol like myo-inositol, typically, at a concentration of about 50-500 mg per liter. In preferred embodiments, the carbon source is sucrose at 3% (w/v).

In some embodiments, the basal media will include gelling agents such as agar, alginic acid, carrageenan, gellangum. Typical concentrations are 0.5-1%. In preferred embodiments, the gelling agent is agar at 0.8%.

Hormones in Media

The present invention requires culturing the *Jatropha* leaf discs in initiation media containing a cytokinin and IBA. The cytokinin is zeatin, kinetin, 1-phenyl-3, 1,2,3 thiadiazol-5-yl urea (thiadiziron), or 6 benzyl amino purine (BAP) alone or in combination with each other. Cytokinin combinations can include BAP alone; TDZ alone; BAP and TDZ; zeatin alone; kinetin alone; zeatin, BAP, and TDZ; kinetin, BAP, and TDZ, etc. In preferred embodiments, the initiation media contains BAP and TDZ.

In preferred embodiments, the method also includes culturing the leaf discs in proliferation and elongation media containing thidiazuron, BAP, gibberelic acid and IBA; and rooting media containing IBA.

In particularly preferred embodiments, the initiation media contains 1-phenyl-3, 1,2,3 thiadiazol-5-yl urea (thidiazuron), 6 benzyl amino purine (BAP), indole butyric acid (IBA); the proliferation and elongation media contains thidiazuron, BAP, gibberelic acid and IBA; and the rooting media contains IBA.

The concentration of the hormones in the invention will differ depending on the media in which it is used and the other hormones in the media.

TDZ preferably ranges from about 0.2 to about 5 µM. Most preferably, the TDZ is at a concentration of about 2.27 µM in the initiation media and about 0.22 µM in the proliferation and elongation media.

BAP preferably ranges from about 2 to about 5 µM. Most preferably, the BAP is at a concentration of about 2.22 µM in the initiation media and about 4.44 µM in the proliferation and elongation media.

Gibberelic acid is preferably at 0.70 µM.

IBA preferably ranges from about 0.1 to about 0.5 µM. Most preferably, the IBA is at about 0.49 µM in the proliferation/elongation media and about 0.41 µM in the rooting media.

Preferred ranges for other cytokinins include 0.2 mg/L to 2.0 mg/L zeatin, 2 mg/L, kinetin at 2.0 mg/l, and 0.5 mg/L to 1.0 mg/L BAP.

Culture Conditions

In certain embodiments, the culture conditions (i.e., light cycle, light intensity, media, temperature, relative humidity) are the same throughout the initiation, proliferation and elongation, and rooting stages. Subculturing is performed as necessary; preferably, every 3 to 4 weeks.

Once well-formed roots are obtained, plantlets can be hardened on soil, sand, moss, charcoal or other media either alone or in combination in defined ratio. The plantlets can then be transferred to the fields by direct sowing or transplanting of the cuttings.

Transformation of Leaf Discs

The availability of a highly efficient regeneration protocol using leaf discs without callus phase is highly desired for genetic transformation. Therefore, the high frequency and efficient regeneration protocol reported here may be as a method to produce transgenics.

In methods of the invention used to generate transgenic *Jatropha*, the leaf disc is transformed prior to micropropagation.

Various methods for the introduction of a desired polynucleotide sequence into leaf discs are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods.

The most commonly used methods for transformation of leaf discs are the *Agrobacterium*-mediated DNA transfer process and the biolistics or microprojectile bombardment mediated process (i.e., the gene gun).

The methods for introducing transgenes into plants by *Agrobacterium*-mediated transformation utilize a T-DNA (transfer DNA) that incorporates the genetic elements of the transgene and transfers those genetic elements into the genome of a plant. Generally, the transgene(s) bordered by a right border DNA molecule (RB) and a left border DNA molecule (LB) is (are) transferred into the plant genome at a single locus. "T-DNA molecule" refers to a DNA molecule that integrates into a plant genome via an *Agrobacterium* mediated transformation method. The ends of the T-DNA molecule are defined in the present invention as being flanked by the border regions of the T-DNA from *Agrobacterium* Ti plasmids. These border regions are generally referred to as the Right border (RB) and Left border (LB) regions and exist as variations in nucleotide sequence and length depending on whether they are derived from nopaline or octopine producing strains of *Agrobacterium*. The border regions commonly used in DNA constructs designed for transferring transgenes into plants are often several hundred polynucleotides in length and comprise a nick site where an endonuclease digests the DNA to provide a site for insertion into the genome of a plant. T-DNA molecules generally contain one or more plant expression cassettes.

With respect to microprojectile bombardment (U.S. Pat. Nos. 5,550,318; 5,538,880; and 5,610,042; each of which is specifically incorporated herein by reference in its entirety), particles are coated with polynucleotides and delivered into cells by a propelling force. Exemplary particles include those containing tungsten, platinum, and preferably, gold. An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Preferred Genes for Transformation

Typically, leaf discs are transformed with genes encoding proteins whose expression confers a desired phenotype. For example, the genes transformed into *Jatropha* can be those implicated in desired elite variety traits, such as dwarf stem, early flowering, synchronous maturity, high seed yield, or high seed oil content. Leaf discs can also be transformed with genes whose transcription in an antisense orientation inhibits the expression of an endogenous gene to achieve a desired phenotypic effect. In some circumstances, leaf discs may also be transformed with genes expressing proteins which are difficult to express in sufficient quantities or at sufficiently high quality in other organisms. Using methods known in the art, these preferred genes are incorporated into vectors suitable for transformation.

Plants of this Invention

Micropropagated true-to-type *Jatropha curcas* plants and transgenic *Jatropha curcas* can be produced using the above described methods. True-to-type plants are generated by selecting a plant and micropropagating a plant from the leaf disc. Transgenic plants are generated by selecting a healthy mother plant, isolating a leaf disc, transforming the leaf disc, and then micropropagating a plant from the leaf disc.

The invention also provides seeds from the plants of this invention and the oil isolated from these seeds using methods known in the art.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Selection of the Mother Plant, Isolation of Embryos and Cotyledons from the Dry Seeds, Culturing Embryo and Cotyledons to Form Seedlings, and Culturing Leaf Discs in Initiation Media Dry seeds were collected from nursery grown plants (2-year-old) raised from vegetative cuttings from selected mother plants. The seeds were dehusked and treated under running tap water for 20-30 min. The de-coated seeds were soaked in distilled water for 24 hours at room temperature. After 24 hours of soaking, de-coated seeds were surface sterilized with 1% (w/v) Bavistin for 30 minutes and subsequently rinsed 3 times with sterile distilled water to remove traces of Bavistin. After treating with Bavistin the seeds were surface sterilized with 0.1% (w/v) mercuric chloride for 6 min followed by sterile distilled water rinsing. The material was blotted dry on sterile filter paper. The endosperm was carefully dissected to expose embryos.

Papery cotyledons including embryo axes were excised and transferred to a 90 mm glass Petri plated containing culture medium. Murashige and Skoog basal salt medium (Ref: Table 2) with 3% sucrose, pH 5.8 and solidified with 0.8% agar was used to grow excised embryos. The culture conditions were maintained at 26+2° C. under a 16/8 photoperiod with cool fluorescent light provided by fluorescent lamps at an intensity of 30 umol/m sub2 S sub 1.

Excised embryos grew into complete plantlets on Murashige and Skoog (Table 2) basal salt medium (Table 2) within 30 days under culture conditions mentioned above. Sixty-day-old complete plantlets with very young leaves were used for the present study.

Very young leaves starting from 1-4 from nodal tips were collected under aseptic conditions and 3-5 mm leaf discs were punched using a sterile stainless steel cork borer. Leaf discs were cultured on MS medium (Table 2) with 3% sucrose (w/v), pH 5.8 and solidified with 0.8% agar. The initiation medium was MS medium supplemented with TDZ (2.27 μM)+BAP (2.22 μM)+IBA (0.49 μM). The cultures were maintained at 26+2° C. in a 16/8 photoperiod with cool, fluorescent light provided by fluorescent lamps at an intensity of 30 umol m sub2 S sub 1.

EXAMPLE 2

Isolation of Leaf Disc from Field-Grown Plants and Culturing Leaf Discs in Initiation Media Individual leaves were carefully isolated from field-grown mother plants and brought to the laboratory. Leaves were washed initially with Tween-20 for 5-6 minutes to dislodge dust particles. After initial washing, leaves were surface sterilized with 1% (w/v) Bavistin for 10 min. followed by three distilled water rinses. After treating with Bavistin, the leaves were subjected to 0.1% (w/v) mercuric chloride treatment for 3 minutes.

3-5 mm leaf discs were punched using standard aseptic stainless steel cork borer and 8 discs were placed on 90 mm glass Petri plate containing MS medium (Table 2) with 3% sucrose (w/v), pH 5.8 and solidified with 0.8% agar supplemented with growth regulators. Leaf discs were cultured on MS medium (Table 2) with 3% sucrose (w/v), pH 5.8 and solidified with 0.8% agar. The initiation medium was MS medium supplemented with TDZ (2.27 μM)+BAP (2.22 μM)+IBA (0.49 μM). The cultures were, maintained at 26+2° C. in 16/8 photoperiod in provided by fluorescent lamps at an intensity of 30 umol m sub2 S sub1.

EXAMPLE 3

Micropropagation of Leaf Explants: Proliferation and Elongation and Rooting Leaf discs were isolated and cultured in initiation media as described in Examples 1 and 2.

The leaf organogenic responses were monitored with regard to the following parameters: leaf discs with callus formation; leaf discs with adventitious buds; and leaf discs with both callus and shoot buds.

The frequency of callus induction and shoot regeneration was recorded after 6 weeks of culture. The cultures were incubated at 20-35° C. under cool, white fluorescent lamps to proliferation and elongation medium supplemented with TDZ (0.22 μM)+BAP (4.44 μM)+IBA (0.50 μM)+Gibberelic Acid (0.70 μM) for a minimum period of 2-3 months to induce shoots with sub-culturing every 30 days.

The cultures were maintained at 26+2° C. in 16/8 photoperiod in provided by fluorescent lamps at an intensity of 30 umol m sub2 S sub1.

Figure 4:
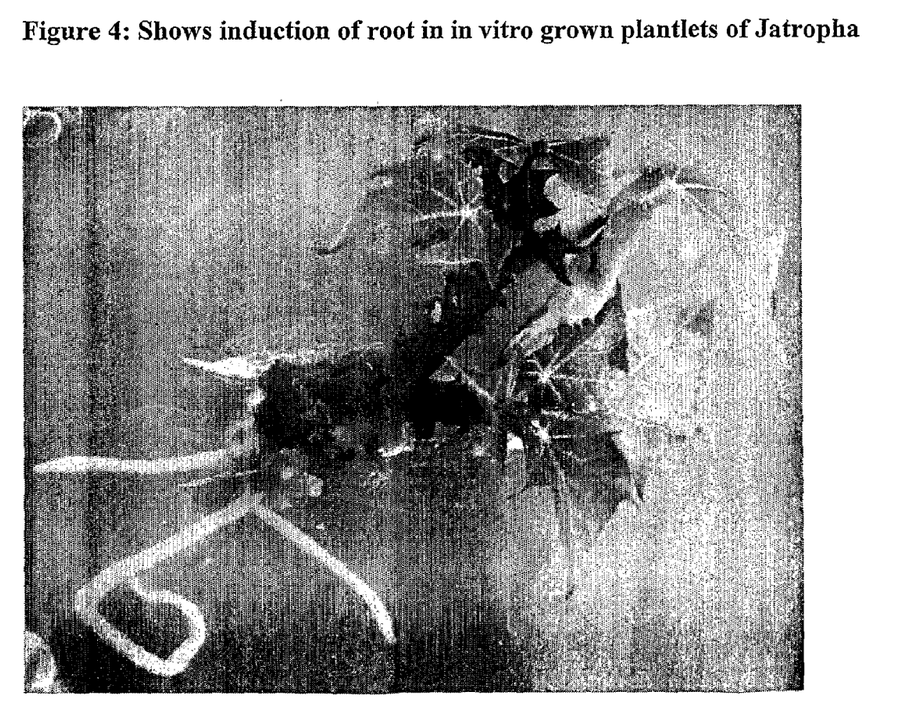
FIG. 4 shows induction of root in in vitro grown plantlets of *Jatropha*.

Well grown shoots of *Jatropha curcas* were separated individually and rooted on full strength MS medium supplemented with IBA (0.41 μM). Rooting was 80% and occurred after 30-45 days of culture without any intermediary callus phase. (FIG. 4)

EXAMPLE 5

Acclimatization of Rooted Shoots

Figure 5:
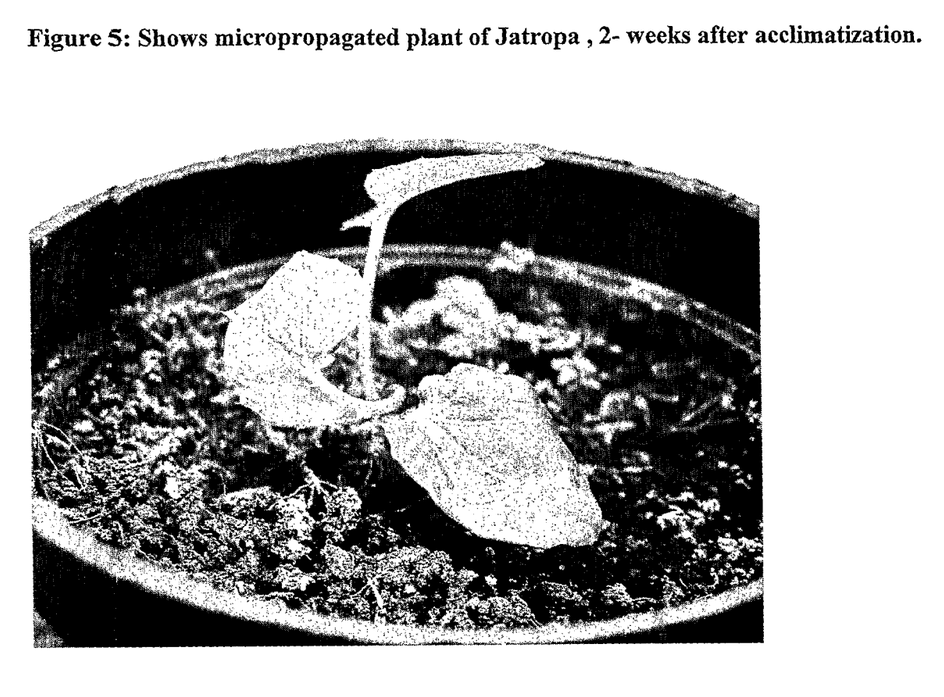
FIG. 5 shows micropropagated plant of *Jatropha* 2 weeks after acclimatization.

The rooted shoots from Example 5 were washed with sterile water to remove agar sticking to the roots and dipped in 0.1% (w/v) Bavistin for 10 min. Well rooted plants of *J. curcas* were transferred to the potting mixture containing 1:1 ratio of cocopeat:garden soil in 3 inch diameter pots. Primary hardening took place for 3-4 weeks in high-humidity conditions. High-humidity conditions were created by placing a polyethene bag over pots. Hardened plants of *J. curcas* were transferred to soil with more than 70% survival after transplantation. (FIG. 5)

EXAMPLE 6

Micropropagated true-to-type *Jatropha curcas* plants were produced and leaf discs were isolated and sterilized using the methods described in Example 1.

Experiments were set-up in a single-factor CRD (one-way ANOVA) to identify the most optimal concentrations of TDZ, BAP, and IBA in the initiation media. Initiated shoots were further propagated as described in the above Examples by being transferred to proliferation and elongation medium which was MS medium (Table 2) with 3% sucrose (w/v), pH 5.8 and solidified with 0.8% agar supplemented with TDZ (0.22 μM)+BAP (4.44 μM)+gibberelic acid (0.70 μM)+IBA (0.50 μM).

All the treatments were performed with 25 replicates, each replication having 8 leaf discs. Data on number of shoots per leaf disc were recorded after 6 weeks of culture.

Leaf discs placed on the various different types of initiation media enlarged and exhibited varied morphological response. Leaf discs cultured on almost all hormonal combinations readily produced hard and compact callus on cut surface within 30 days of culture. The adventitious bud induction from leaf disc explants was studied in presence of various concentrations of TDZ and BAP as a source of cytokinin along with very low levels of IBA.

When cytokinins (TDA and BAP) were used individually, i.e., TDZ (at 2.27 μM or 4.55 μM) or BAP (at 2.22 μM or 4.44 μM), along with lower levels of IBA, callus induction was prominent (Table 1). BAP (4.44 μM) along with IBA (2.46 μM) induced callus in 62% of explants. TDZ (at 2.27 μM) along with IBA (0.49 μM) induced callus in 52.5% of explants.

Figure 1:
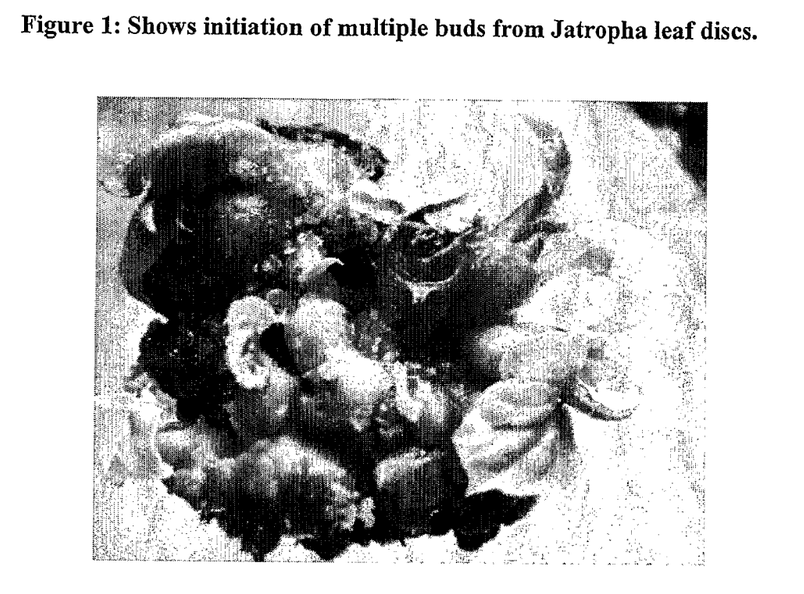
FIG. 1 shows initiation of multiple buds from *Jatropha* leaf discs.
Figure 2:
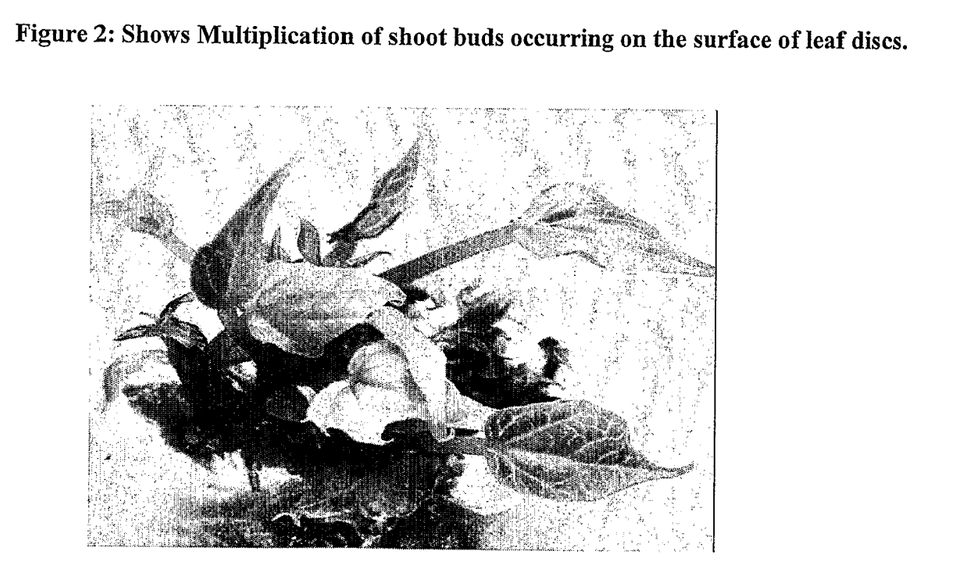
FIG. 2 shows multiplication of shoot buds occurring on the surface of leaf discs.
Figure 3:
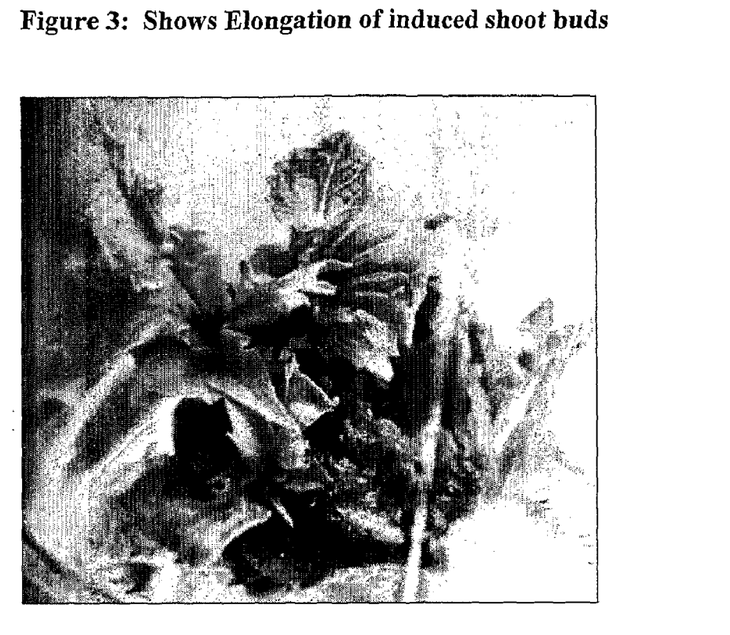
FIG. 3 shows elongation of induced shoot buds.

However, when TDZ and BAP together were used in combination along with IBA there was a marked difference in morphological response. The adventitious bud induction from leaf disc explant was more prominent in presence of TDZ (2.27 μM or 4.55 μM) and BAP (2.22 μM or 4.44 μM). When added together, they induced bud induction in 53.5% of explants. Lower levels of TDZ and BAP were found to be more effective in terms of adventitious bud induction than higher levels of TDZ and BAP. TDZ was also found to be more effective over BAP in terms of bud induction, as BAP induced callus from leaf disc explants. The total number of shoot bud induction per leaf disc in TDZ treatment ranged between 4-20 buds (FIG. 1).

This example demonstrates that TDZ (2.27 μM)+BAP (2.22 μM) in combination with IBA (0.49 μM) is suitable for in vitro propagation of *J. curcas* through direct regeneration from leaf discs.

TABLE 1

Effect of plant growth regulator concentrations on adventitious bud induction and callus formation from Jatropha leaf disc explants.

| | PGR Concentration (μM) | | | Response of leaf disc explants (%) | | |
|---|---|---|---|---|---|---|
| Sr. No. | TDZ | BAP | IBA | Callus formation | Bud Induction | Non-responsive |
| 1 | 2.27 | 2.22 | 0.49 | 40 e | 53.5 a (47.040) | 6.5 (2.160) |
| 2 | 4.55 | 4.44 | 0.98 | 50 de | 37 bc (37.320) | 13 (3.376) |
| 3 | 2.27 | — | 0.49 | 52.5 cd | 24.5 d (29.328) | 23 (4.767) |
| 4 | 4.55 | — | 2.46 | 50 de | 32 bc (34.368) | 18 (4.244) |
| 5 | — | 2.22 | 0.49 | 58 abc | 12 f (21.072) | 30 (5.435) |
| 6 | — | 4.44 | 2.46 | 62 a | 20 e (26.220) | 18 (4.100) |

The figures in the parenthesis are arcsine angular transformation values (for bud induction) and square root transformation values (for non-responsive).

| | | | |
|---|---|---|---|
| S.E. ± | 2.436 | 1.086 | 0.242 |
| C.D. at 5% | 6.809 | 3.036 | 0.676 |
| C.V.(%) | 23.386 | 16.674 | 30.125 |

Data scored after 6 weeks of culture inoculation.
Experimental Design: single factor CRD (One-way ANOVA) No. of explants used to calculate the means: 200 (8 leaf disc explant/replication and 25 replications. Means in each column followed by same letters are not significantly different.

TABLE 2

Murashige and Skoog Medium (1962)

| Component | Concentration (mg/l) |
|---|---|
| $NH_4NO_3$ | 1650 |
| $KNO_3$ | 1900 |
| $CaCl_2 \cdot 2H_2O$ | 440 |
| $MgSO_4 \cdot 7H_2O$ | 370 |
| $KH_2PO_4$ | 170 |
| KI | 0.83 |
| $H_3BO_3$ | 6.2 |
| $MnSO_4 \cdot 4H_2O$ | 22.3 |
| $ZnSO_4 \cdot 7H_2O$ | 8.6 |
| $Na_2MoO_4 \cdot 2H_2O$ | 0.25 |
| $CuSO_4 \cdot 5H_2O$ | 0.025 |
| $CoCl_2 \cdot 6H_2O$ | 0.025 |
| $FeSO_4 \cdot 7H_2O$ | 27.8 |
| $Na_2EDTA \cdot 2H_2O$ | 37.3 |
| Glycine | 2.0 |
| Myo-inositol | 100.0 |
| Nicotinic acid | 0.5 |
| Pyridoxine HCl | 0.5 |
| Thiamine HCl | 0.1 |
| pH of the medium | 5.8 |

REFERENCES

1. Tsugawa, H; Kagami, T and Suzuki, M (2004). High-frequency transformation of Lobelia erinus L by *Agrobacterium* mediated gene transfer. Plant Cell Rep. Vol. 22 (10), pp. 759-764.
2. Srivastava, P. S (1974). In vitro induction of triploid roots and shoots from mature endosperm of *Jatropha panduraefolia*. Z. Pflanzenphysiol. Vol. 66, pp. 93-96.
3. Srivastava, P. S and Johri, B. M (1974). Morphogenesis in mature endosperm cultures of *Jatropha panduraefolia*, Beitr. Biol. Pflanz. Vol. 50, pp. 255-268.
4. Sujatha, M and Dhingra, M (1993). Rapid plant regeneration from various explants of *Jatropha integerrima*. Plant Cell Tiss. Org. Cult. Vol. 35, pp. 293-296.
5. Sujatha, M and Mukta, N (1996). Morphogenesis and plant regeneration from tissue cultures of *Jatropha curcas*. Plant Cell Tiss. Org. Cult. Vol. 44, pp. 135-141.
6. Weida, L; Qim, W; Lin, Tang; Fang, Y and Fang, C (2003). Induction of callus from *Jatropha curcas* and its rapid propagation. Yingyong Yu Huanjing Shengwu Xuebao, Vol. 9 (2), pp. 127-130.
7. Johri, B. M and Srivastava, P. S (1973). Morphogenesis in endosperm cultures. Z. Pflanzenphysiol. Vol. 70, pp. 285-304
8. Chandran, K and Sujatha M (1996). Isolation and purification of protoplasts of castor (*Ricinus communis* L) and *Jatropha* spp. GAU Res. J. Vol. 21, pp. 110-111.

All of the references cited herein are hereby incorporated by reference.

Thus, while we have described fundamental novel features of the invention, it will be understood that various omissions and substitutions and changes in the form and details may be possible without departing from the spirit of the invention. For example, it is expressly intended that all combinations of those elements and/or method steps, which perform substantially the same function in substantially the same way to achieve the same results, are within the scope of the invention.

The invention claimed is:

1. A method for producing a micropropagated true-to-type *Jatropha curcas* plant, comprising the steps of:
    selecting a leaf from a *Jatropha curcas* plant,
    isolating a leaf disc from the leaf, and
    micropropagating the leaf disc in
    shoot initiation media comprising 1-phenyl-3,1,2,3thiadiazol-5-yl urea (thidiazuron), 6 benzyl amino purine (BAP), and indole butyric acid (IBA);
    proliferation and elongation media comprising thidiazuron, BAP, gibberellic acid and IBA; and
    rooting media comprising IBA
    to produce the micropropagated true-to-type *Jatropha curcas* plant without passing through a callus phase.

2. The method of claim 1, wherein the leaf is treated to reduce microbial contamination.

3. The method of claim 1, wherein the leaf disc is treated to reduce microbial contamination.

4. The method of claim 1, wherein the initiation media comprises thidiazuron at a concentration of about 2.27 µM, BAP at concentration of about 2.22 µM and IBA at a concentration of about 0.49 µM.

5. The method of claim 1, wherein the proliferation and elongation media comprises thidiazuron at a concentration of about 0.22 µM, BAP at a concentration of about 4.44 µM, gibberellic acid at a concentration of about 0.70 µM, and IBA at a concentration of about 0.50 µM.

6. The method of claim 1, wherein the rooting media comprises IBA at a concentration of about 0.41 µM.

7. The method of claim 1, wherein the selected *Jatropha curcas* plant is a field grown plant.

8. The method of claim 1, wherein the selected *Jatropha curcas* plant is a micropropagated plant.

9. The method of claim 1, wherein the isolated leaf is a young leaf.

10. The method of claim 9, wherein the young leaf is selected from the group consisting of: a second leaf, a third leaf, and a fourth leaf.

11. The method of claim 9, wherein the young leaf is a third leaf.

12. The method of claim 1, wherein the *Jatropha curcas* plant is an elite variety.

* * * * *